(12) United States Patent
Tsukada

(10) Patent No.: US 8,041,512 B2
(45) Date of Patent: Oct. 18, 2011

(54) METHOD OF ACQUIRING A SET OF SPECIFIC ELEMENTS FOR DISCRIMINATING SEQUENCE

(75) Inventor: Mamoru Tsukada, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 307 days.

(21) Appl. No.: 11/015,003

(22) Filed: Dec. 20, 2004

(65) Prior Publication Data

US 2005/0143930 A1 Jun. 30, 2005

(30) Foreign Application Priority Data

Dec. 26, 2003 (JP) ................................ 2003-434554

(51) Int. Cl.
*G01N 33/48* (2006.01)
*C12Q 1/68* (2006.01)
*G06G 7/58* (2006.01)
(52) U.S. Cl. .................. 702/19; 435/6; 702/20; 703/11
(58) Field of Classification Search .......................... None
See application file for complete search history.

(56) References Cited

U.S. PATENT DOCUMENTS

| 7,254,488 | B2 | 8/2007 | Yoshii | |
| 2004/0241643 | A1 | 12/2004 | Yamamoto et al. | 435/5 |

FOREIGN PATENT DOCUMENTS

| JP | 2003-280 A | 1/2003 |
| JP | 2003-038160 | 2/2003 |
| WO | WO-9710365 A1 * | 3/1997 |
| WO | 02/10443 A1 | 2/2002 |

OTHER PUBLICATIONS

Thompson et al. et al., Nucleic Acid Research, vol. 25, pp. 4876-4882.*
Thompson et al., Nucleic Acids Research, vol. 25, pp. 4876-4882, 1997.*
Tyler, E. C., et al., "A Review of Algorithms for Molecular Sequence Comparison", Computers and Biomedical Research, vol. 24, No. 1 (Feb. 1991), pp. 72-96.
DeSantis, et al., "Comprehensive aligned sequence construction for automated design of effective probes (CASCADE-P) using 16S rDNA", Bioinformatics, vol. 19, No. 12, 2003, pp. 1461-1468.
Schliep, et al., "Group Testing With DNA Chips: Generating Designs and Decoding Experiments", Proceedings of the Computational Systems Bioinformatics (CSB '03), 2003, pp. 1-8.

* cited by examiner

*Primary Examiner* — Shubo Zhou
(74) *Attorney, Agent, or Firm* — Fitzpatrick, Cella, Harper & Scinto

(57) ABSTRACT

To provide a method of accurately and efficiently acquiring a candidate for a set of discrimination elements for identification. Provided is a method of acquiring a set of specific elements on a specific sequence for discriminating the specific sequence from a number of sequences, including the steps of acquiring a group of alignment data in which each of the number of sequences is subjected to alignment processing, and acquiring a set of elements capable of discriminating the specific sequence through computational processing on the group of alignment data.

6 Claims, 1 Drawing Sheet

SEQUENCE LISTING

<160> NUMBER OF SEQ ID NOS: 81

<210> SEQ ID NO 1

```
<211> LENGTH: 20
<212> TYPE: DNA
<213> ORGANISM: Artificial
<220> FEATURE:
<223> OTHER INFORMATION: Synthesized DNA probe

<400> SEQUENCE: 1
atctataacc aagaggagtc                                              20

<210> SEQ ID NO 2
<211> LENGTH: 16
<212> TYPE: DNA
<213> ORGANISM: Artificial
<220> FEATURE:
<223> OTHER INFORMATION: Synthesized DNA probe

<400> SEQUENCE: 2
gctggggcgg cctgat                                                  16

<210> SEQ ID NO 3
<211> LENGTH: 16
<212> TYPE: DNA
<213> ORGANISM: Artificial
<220> FEATURE:
<223> OTHER INFORMATION: Synthesized DNA probe

<400> SEQUENCE: 3
ggggcggcct gatgcc                                                  16

<210> SEQ ID NO 4
<211> LENGTH: 18
<212> TYPE: DNA
<213> ORGANISM: Artificial
<220> FEATURE:
<223> OTHER INFORMATION: Synthesized DNA probe

<400> SEQUENCE: 4
ggaacagcca gaaggacc                                                18

<210> SEQ ID NO 5
<211> LENGTH: 17
<212> TYPE: DNA
<213> ORGANISM: Artificial
<220> FEATURE:
<223> OTHER INFORMATION: Synthesized DNA probe

<400> SEQUENCE: 5
gacctcctgg agcagag                                                 17

<210> SEQ ID NO 6
<211> LENGTH: 18
<212> TYPE: DNA
<213> ORGANISM: Artificial
<220> FEATURE:
<223> OTHER INFORMATION: Synthesized DNA probe

<400> SEQUENCE: 6
cacaactacg gggttggt                                                18

<210> SEQ ID NO 7
<211> LENGTH: 20
<212> TYPE: DNA
<213> ORGANISM: Artificial
<220> FEATURE:
<223> OTHER INFORMATION: Synthesized DNA probe

<400> SEQUENCE: 7
```

-continued

```
<210> SEQ ID NO 8
<211> LENGTH: 16
<212> TYPE: DNA
<213> ORGANISM: Artificial
<220> FEATURE:
<223> OTHER INFORMATION: Synthesized DNA probe

<400> SEQUENCE: 8
agcagaagcg gggccg                                                      16

<210> SEQ ID NO 9
<211> LENGTH: 18
<212> TYPE: DNA
<213> ORGANISM: Artificial
<220> FEATURE:
<223> OTHER INFORMATION: Synthesized DNA probe

<400> SEQUENCE: 9
cacaactacg gggttgtg                                                    18

<210> SEQ ID NO 10
<211> LENGTH: 17
<212> TYPE: DNA
<213> ORGANISM: Artificial
<220> FEATURE:
<223> OTHER INFORMATION: Synthesized DNA probe

<400> SEQUENCE: 10
ggggccgggt ggacaat                                                     17

<210> SEQ ID NO 11
<211> LENGTH: 20
<212> TYPE: DNA
<213> ORGANISM: Artificial
<220> FEATURE:
<223> OTHER INFORMATION: Synthesized DNA probe

<400> SEQUENCE: 11
cctggacaga tacttctatc                                                  20

<210> SEQ ID NO 12
<211> LENGTH: 18
<212> TYPE: DNA
<213> ORGANISM: Artificial
<220> FEATURE:
<223> OTHER INFORMATION: Synthesized DNA probe

<400> SEQUENCE: 12
ggacctcctg gagcagaa                                                    18

<210> SEQ ID NO 13
<211> LENGTH: 21
<212> TYPE: DNA
<213> ORGANISM: Artificial
<220> FEATURE:
<223> OTHER INFORMATION: Synthesized DNA probe

<400> SEQUENCE: 13
agatacttct atcaccaaga a                                                21

<210> SEQ ID NO 14
<211> LENGTH: 20
<212> TYPE: DNA
<213> ORGANISM: Artificial
<220> FEATURE:
```

<223> OTHER INFORMATION: Synthesized DNA probe

<400> SEQUENCE: 14
ttctatcacc aagaggagta                   20

<210> SEQ ID NO 15
<211> LENGTH: 16
<212> TYPE: DNA
<213> ORGANISM: Artificial
<220> FEATURE:
<223> OTHER INFORMATION: Synthesized DNA probe

<400> SEQUENCE: 15
agcagaggcg ggccga                       16

<210> SEQ ID NO 16
<211> LENGTH: 16
<212> TYPE: DNA
<213> ORGANISM: Artificial
<220> FEATURE:
<223> OTHER INFORMATION: Synthesized DNA probe

<400> SEQUENCE: 16
ggggcggcct gacgct                       16

<210> SEQ ID NO 17
<211> LENGTH: 16
<212> TYPE: DNA
<213> ORGANISM: Artificial
<220> FEATURE:
<223> OTHER INFORMATION: Synthesized DNA probe

<400> SEQUENCE: 17
agctggggcg gcctag                       16

<210> SEQ ID NO 18
<211> LENGTH: 18
<212> TYPE: DNA
<213> ORGANISM: Artificial
<220> FEATURE:
<223> OTHER INFORMATION: Synthesized DNA probe

<400> SEQUENCE: 18
caagaggagt acgtgcgg                     18

<210> SEQ ID NO 19
<211> LENGTH: 18
<212> TYPE: DNA
<213> ORGANISM: Artificial
<220> FEATURE:
<223> OTHER INFORMATION: Synthesized DNA probe

<400> SEQUENCE: 19
gacctcctgg agcagaga                     18

<210> SEQ ID NO 20
<211> LENGTH: 17
<212> TYPE: DNA
<213> ORGANISM: Artificial
<220> FEATURE:
<223> OTHER INFORMATION: Synthesized DNA probe

<400> SEQUENCE: 20
gggcggtgac ggagcta                      17

<210> SEQ ID NO 21

```
<211> LENGTH: 19
<212> TYPE: DNA
<213> ORGANISM: Artificial
<220> FEATURE:
<223> OTHER INFORMATION: Synthesized DNA probe

<400> SEQUENCE: 21
tttcctgtgg cagggtaaa                                                  19

<210> SEQ ID NO 22
<211> LENGTH: 21
<212> TYPE: DNA
<213> ORGANISM: Artificial
<220> FEATURE:
<223> OTHER INFORMATION: Synthesized DNA probe

<400> SEQUENCE: 22
cttctataac caagaggagt a                                               21

<210> SEQ ID NO 23
<211> LENGTH: 18
<212> TYPE: DNA
<213> ORGANISM: Artificial
<220> FEATURE:
<223> OTHER INFORMATION: Synthesized DNA probe

<400> SEQUENCE: 23
ggaacagcca gaaggact                                                   18

<210> SEQ ID NO 24
<211> LENGTH: 17
<212> TYPE: DNA
<213> ORGANISM: Artificial
<220> FEATURE:
<223> OTHER INFORMATION: Synthesized DNA probe

<400> SEQUENCE: 24
gaagacaggc gggccct                                                    17

<210> SEQ ID NO 25
<211> LENGTH: 17
<212> TYPE: DNA
<213> ORGANISM: Artificial
<220> FEATURE:
<223> OTHER INFORMATION: Synthesized DNA probe

<400> SEQUENCE: 25
agtaccgggc ggtgaca                                                    17

<210> SEQ ID NO 26
<211> LENGTH: 19
<212> TYPE: DNA
<213> ORGANISM: Artificial
<220> FEATURE:
<223> OTHER INFORMATION: Synthesized DNA probe

<400> SEQUENCE: 26
tccataacca ggaggagtt                                                  19

<210> SEQ ID NO 27
<211> LENGTH: 17
<212> TYPE: DNA
<213> ORGANISM: Artificial
<220> FEATURE:
<223> OTHER INFORMATION: Synthesized DNA probe

<400> SEQUENCE: 27
```
cggagcgggt gcggtat                                            17

<210> SEQ ID NO 28
<211> LENGTH: 16
<212> TYPE: DNA
<213> ORGANISM: Artificial
<220> FEATURE:
<223> OTHER INFORMATION: Synthesized DNA probe

<400> SEQUENCE: 28
cctggagcgg aggcgt                                             16

<210> SEQ ID NO 29
<211> LENGTH: 18
<212> TYPE: DNA
<213> ORGANISM: Artificial
<220> FEATURE:
<223> OTHER INFORMATION: Synthesized DNA probe

<400> SEQUENCE: 29
ggttgctgga aagacgcg                                           18

<210> SEQ ID NO 30
<211> LENGTH: 16
<212> TYPE: DNA
<213> ORGANISM: Artificial
<220> FEATURE:
<223> OTHER INFORMATION: Synthesized DNA probe

<400> SEQUENCE: 30
cctggagcgg aggcgc                                             16

<210> SEQ ID NO 31
<211> LENGTH: 17
<212> TYPE: DNA
<213> ORGANISM: Artificial
<220> FEATURE:
<223> OTHER INFORMATION: Synthesized DNA probe

<400> SEQUENCE: 31
ctggggcggc ctgatga                                            17

<210> SEQ ID NO 32
<211> LENGTH: 17
<212> TYPE: DNA
<213> ORGANISM: Artificial
<220> FEATURE:
<223> OTHER INFORMATION: Synthesized DNA probe

<400> SEQUENCE: 32
tcctggaaga caggcgc                                            17

<210> SEQ ID NO 33
<211> LENGTH: 20
<212> TYPE: DNA
<213> ORGANISM: Artificial
<220> FEATURE:
<223> OTHER INFORMATION: Synthesized DNA probe

<400> SEQUENCE: 33
ctgagtgtca tttcttcaac                                         20

<210> SEQ ID NO 34
<211> LENGTH: 18
<212> TYPE: DNA
<213> ORGANISM: Artificial
<220> FEATURE:

<223> OTHER INFORMATION: Synthesized DNA probe

<400> SEQUENCE: 34
tccataacca ggaggagc                                              18

<210> SEQ ID NO 35
<211> LENGTH: 18
<212> TYPE: DNA
<213> ORGANISM: Artificial
<220> FEATURE:
<223> OTHER INFORMATION: Synthesized DNA probe

<400> SEQUENCE: 35
ggaacagcca gaaggaca                                              18

<210> SEQ ID NO 36
<211> LENGTH: 17
<212> TYPE: DNA
<213> ORGANISM: Artificial
<220> FEATURE:
<223> OTHER INFORMATION: Synthesized DNA probe

<400> SEQUENCE: 36
ccgcggtgga cacctat                                               17

<210> SEQ ID NO 37
<211> LENGTH: 18
<212> TYPE: DNA
<213> ORGANISM: Artificial
<220> FEATURE:
<223> OTHER INFORMATION: Synthesized DNA probe

<400> SEQUENCE: 37
aggacatcct ggaagacg                                              18

<210> SEQ ID NO 38
<211> LENGTH: 18
<212> TYPE: DNA
<213> ORGANISM: Artificial
<220> FEATURE:
<223> OTHER INFORMATION: Synthesized DNA probe

<400> SEQUENCE: 38
ggacatcctg gaagacga                                              18

<210> SEQ ID NO 39
<211> LENGTH: 17
<212> TYPE: DNA
<213> ORGANISM: Artificial
<220> FEATURE:
<223> OTHER INFORMATION: Synthesized DNA probe

<400> SEQUENCE: 39
tggaagacga gcgggct                                               17

<210> SEQ ID NO 40
<211> LENGTH: 17
<212> TYPE: DNA
<213> ORGANISM: Artificial
<220> FEATURE:
<223> OTHER INFORMATION: Synthesized DNA probe

<400> SEQUENCE: 40
tcctggaaga cgagcgc                                               17

<210> SEQ ID NO 41

<211> LENGTH: 19
<212> TYPE: DNA
<213> ORGANISM: Artificial
<220> FEATURE:
<223> OTHER INFORMATION: Synthesized DNA probe

<400> SEQUENCE: 41
tcttggagta ctctacgtc                                                    19

<210> SEQ ID NO 42
<211> LENGTH: 19
<212> TYPE: DNA
<213> ORGANISM: Artificial
<220> FEATURE:
<223> OTHER INFORMATION: Synthesized DNA probe

<400> SEQUENCE: 42
cggttcctgg acagatact                                                    19

<210> SEQ ID NO 43
<211> LENGTH: 19
<212> TYPE: DNA
<213> ORGANISM: Artificial
<220> FEATURE:
<223> OTHER INFORMATION: Synthesized DNA probe

<400> SEQUENCE: 43
gaaggacttc ctggaagac                                                    19

<210> SEQ ID NO 44
<211> LENGTH: 16
<212> TYPE: DNA
<213> ORGANISM: Artificial
<220> FEATURE:
<223> OTHER INFORMATION: Synthesized DNA probe

<400> SEQUENCE: 44
cggcctgctg cggagc                                                       16

<210> SEQ ID NO 45
<211> LENGTH: 18
<212> TYPE: DNA
<213> ORGANISM: Artificial
<220> FEATURE:
<223> OTHER INFORMATION: Synthesized DNA probe

<400> SEQUENCE: 45
gccgaggtgg acacctat                                                     18

<210> SEQ ID NO 46
<211> LENGTH: 20
<212> TYPE: DNA
<213> ORGANISM: Artificial
<220> FEATURE:
<223> OTHER INFORMATION: Synthesized DNA probe

<400> SEQUENCE: 46
cgtttcttgg agtactctac                                                   20

<210> SEQ ID NO 47
<211> LENGTH: 17
<212> TYPE: DNA
<213> ORGANISM: Artificial
<220> FEATURE:
<223> OTHER INFORMATION: Synthesized DNA probe

<400> SEQUENCE: 47

-continued gggtgcggtt cctggag                                                    17

<210> SEQ ID NO 48
<211> LENGTH: 20
<212> TYPE: DNA
<213> ORGANISM: Artificial
<220> FEATURE:
<223> OTHER INFORMATION: Synthesized DNA probe

<400> SEQUENCE: 48
agagatactt ccataaccag                                                 20

<210> SEQ ID NO 49
<211> LENGTH: 19
<212> TYPE: DNA
<213> ORGANISM: Artificial
<220> FEATURE:
<223> OTHER INFORMATION: Synthesized DNA probe

<400> SEQUENCE: 49
ttccataacc aggaggaga                                                  19

<210> SEQ ID NO 50
<211> LENGTH: 19
<212> TYPE: DNA
<213> ORGANISM: Artificial
<220> FEATURE:
<223> OTHER INFORMATION: Synthesized DNA probe

<400> SEQUENCE: 50
tccataacca ggaggagaa                                                  19

<210> SEQ ID NO 51
<211> LENGTH: 19
<212> TYPE: DNA
<213> ORGANISM: Artificial
<220> FEATURE:
<223> OTHER INFORMATION: Synthesized DNA probe

<400> SEQUENCE: 51
ctctacgtct gagtgtcaa                                                  19

<210> SEQ ID NO 52
<211> LENGTH: 16
<212> TYPE: DNA
<213> ORGANISM: Artificial
<220> FEATURE:
<223> OTHER INFORMATION: Synthesized DNA probe

<400> SEQUENCE: 52
ggggcggcct gatgct                                                     16

<210> SEQ ID NO 53
<211> LENGTH: 18
<212> TYPE: DNA
<213> ORGANISM: Artificial
<220> FEATURE:
<223> OTHER INFORMATION: Synthesized DNA probe

<400> SEQUENCE: 53
cagacacaac tacggggc                                                   18

<210> SEQ ID NO 54
<211> LENGTH: 17
<212> TYPE: DNA
<213> ORGANISM: Artificial
<220> FEATURE:

```
<223> OTHER INFORMATION: Synthesized DNA probe

<400> SEQUENCE: 54
agcgacgtgg gggagtt                                                    17

<210> SEQ ID NO 55
<211> LENGTH: 17
<212> TYPE: DNA
<213> ORGANISM: Artificial
<220> FEATURE:
<223> OTHER INFORMATION: Synthesized DNA probe

<400> SEQUENCE: 55
gacatcctgg agcaggc                                                    17

<210> SEQ ID NO 56
<211> LENGTH: 19
<212> TYPE: DNA
<213> ORGANISM: Artificial
<220> FEATURE:
<223> OTHER INFORMATION: Synthesized DNA probe

<400> SEQUENCE: 56
ctgcagacac aactacgga                                                  19

<210> SEQ ID NO 57
<211> LENGTH: 19
<212> TYPE: DNA
<213> ORGANISM: Artificial
<220> FEATURE:
<223> OTHER INFORMATION: Synthesized DNA probe

<400> SEQUENCE: 57
acacaactac ggagttgtg                                                  19

<210> SEQ ID NO 58
<211> LENGTH: 21
<212> TYPE: DNA
<213> ORGANISM: Artificial
<220> FEATURE:
<223> OTHER INFORMATION: Synthesized DNA probe

<400> SEQUENCE: 58
ctggacagat acttctataa t                                               21

<210> SEQ ID NO 59
<211> LENGTH: 18
<212> TYPE: DNA
<213> ORGANISM: Artificial
<220> FEATURE:
<223> OTHER INFORMATION: Synthesized DNA probe

<400> SEQUENCE: 59
ctgtggcagc ctaagagg                                                   18

<210> SEQ ID NO 60
<211> LENGTH: 18
<212> TYPE: DNA
<213> ORGANISM: Artificial
<220> FEATURE:
<223> OTHER INFORMATION: Synthesized DNA probe

<400> SEQUENCE: 60
aaggacctcc tggaagac                                                   18

<210> SEQ ID NO 61
```

```
<211> LENGTH: 16
<212> TYPE: DNA
<213> ORGANISM: Artificial
<220> FEATURE:
<223> OTHER INFORMATION: Synthesized DNA probe

<400> SEQUENCE: 61
gctggggcgg cctgtc                                                    16

<210> SEQ ID NO 62
<211> LENGTH: 16
<212> TYPE: DNA
<213> ORGANISM: Artificial
<220> FEATURE:
<223> OTHER INFORMATION: Synthesized DNA probe

<400> SEQUENCE: 62
ggcctgtcgc cgagtc                                                    16

<210> SEQ ID NO 63
<211> LENGTH: 17
<212> TYPE: DNA
<213> ORGANISM: Artificial
<220> FEATURE:
<223> OTHER INFORMATION: Synthesized DNA probe

<400> SEQUENCE: 63
cggcctgttg ccgagtc                                                   17

<210> SEQ ID NO 64
<211> LENGTH: 17
<212> TYPE: DNA
<213> ORGANISM: Artificial
<220> FEATURE:
<223> OTHER INFORMATION: Synthesized DNA probe

<400> SEQUENCE: 64
gagtaccggg cggtgag                                                   17

<210> SEQ ID NO 65
<211> LENGTH: 17
<212> TYPE: DNA
<213> ORGANISM: Artificial
<220> FEATURE:
<223> OTHER INFORMATION: Synthesized DNA probe

<400> SEQUENCE: 65
ggggccaggt ggacaat                                                   17

<210> SEQ ID NO 66
<211> LENGTH: 19
<212> TYPE: DNA
<213> ORGANISM: Artificial
<220> FEATURE:
<223> OTHER INFORMATION: Synthesized DNA probe

<400> SEQUENCE: 66
ggtggacaat tactgcagg                                                 19

<210> SEQ ID NO 67
<211> LENGTH: 16
<212> TYPE: DNA
<213> ORGANISM: Artificial
<220> FEATURE:
<223> OTHER INFORMATION: Synthesized DNA probe

<400> SEQUENCE: 67
```

```
ggggcggcct gatgcg                                                16
```

<210> SEQ ID NO 68
<211> LENGTH: 17
<212> TYPE: DNA
<213> ORGANISM: Artificial
<220> FEATURE:
<223> OTHER INFORMATION: Synthesized DNA probe

<400> SEQUENCE: 68

```
gagcagaagc ggggcca                                               17
```

<210> SEQ ID NO 69
<211> LENGTH: 18
<212> TYPE: DNA
<213> ORGANISM: Artificial
<220> FEATURE:
<223> OTHER INFORMATION: Synthesized DNA probe

<400> SEQUENCE: 69

```
tgcagacaca actacggc                                              18
```

<210> SEQ ID NO 70
<211> LENGTH: 15
<212> TYPE: DNA
<213> ORGANISM: Artificial
<220> FEATURE:
<223> OTHER INFORMATION: Synthesized DNA probe

<400> SEQUENCE: 70

```
gcgggccgag gtggg                                                 15
```

<210> SEQ ID NO 71
<211> LENGTH: 20
<212> TYPE: DNA
<213> ORGANISM: Artificial
<220> FEATURE:
<223> OTHER INFORMATION: Synthesized DNA probe

<400> SEQUENCE: 71

```
taagtgtgag tgtcatttcc                                            20
```

<210> SEQ ID NO 72
<211> LENGTH: 18
<212> TYPE: DNA
<213> ORGANISM: Artificial
<220> FEATURE:
<223> OTHER INFORMATION: Synthesized DNA probe

<400> SEQUENCE: 72

```
gcgcgctaca acagtgat                                              18
```

<210> SEQ ID NO 73
<211> LENGTH: 20
<212> TYPE: DNA
<213> ORGANISM: Artificial
<220> FEATURE:
<223> OTHER INFORMATION: Synthesized DNA probe

<400> SEQUENCE: 73

```
ctataaccaa gaggaggact                                            20
```

<210> SEQ ID NO 74
<211> LENGTH: 17
<212> TYPE: DNA
<213> ORGANISM: Artificial
<220> FEATURE:

<223> OTHER INFORMATION: Synthesized DNA probe

<400> SEQUENCE: 74
gcggttcctg cacagag                                                    17

<210> SEQ ID NO 75
<211> LENGTH: 20
<212> TYPE: DNA
<213> ORGANISM: Artificial
<220> FEATURE:
<223> OTHER INFORMATION: Synthesized DNA probe

<400> SEQUENCE: 75
catctataac caagaggaga                                                 20

<210> SEQ ID NO 76
<211> LENGTH: 18
<212> TYPE: DNA
<213> ORGANISM: Artificial
<220> FEATURE:
<223> OTHER INFORMATION: Synthesized DNA probe

<400> SEQUENCE: 76
cacaactacg gggctgtg                                                   18

<210> SEQ ID NO 77
<211> LENGTH: 24
<212> TYPE: DNA
<213> ORGANISM: Artificial
<220> FEATURE:
<223> OTHER INFORMATION: Synthesized DNA probe

<400> SEQUENCE: 77
ttgctggaca gatgcatcca taac                                            24

<210> SEQ ID NO 78
<211> LENGTH: 24
<212> TYPE: DNA
<213> ORGANISM: Artificial
<220> FEATURE:
<223> OTHER INFORMATION: Synthesized DNA probe

<400> SEQUENCE: 78
tacctggaca gatacttcca tgac                                            24

<210> SEQ ID NO 79
<211> LENGTH: 24
<212> TYPE: DNA
<213> ORGANISM: Artificial
<220> FEATURE:
<223> OTHER INFORMATION: Synthesized DNA probe

<400> SEQUENCE: 79
tacctggaca gatccttcca taac                                            24

<210> SEQ ID NO 80
<211> LENGTH: 24
<212> TYPE: DNA
<213> ORGANISM: Artificial
<220> FEATURE:
<223> OTHER INFORMATION: Synthesized DNA probe

<400> SEQUENCE: 80
tacctggaca gatccttcca taac                                            24

<210> SEQ ID NO 81

-continued

```
<211> LENGTH: 24
<212> TYPE: DNA
<213> ORGANISM: Artificial
<220> FEATURE:
<223> OTHER INFORMATION: Synthesized DNA probe

<400> SEQUENCE: 81
tagctggaca gatacttcca tgac                                              24
```

METHOD OF ACQUIRING A SET OF SPECIFIC ELEMENTS FOR DISCRIMINATING SEQUENCE

BACKGROUND OF THE INVENTION

1. Field of the Invention

The present invention relates to an information processing method of acquiring an element (such as a character or a symbol at a specific position) that characterizes a specific sequence from multiple pieces of sequence information, and preferably to a technique for processing sequence information such as a base sequence or an amino acid sequence.

2. Related Background Art

In recent years, there are needs for SNPs, polymorphism analysis, and the like to discriminate and identify different nucleic acid sequences according to a method such as hybridization or PCR. To that end, an element for discrimination and identification must be extracted first and a probe (or primer) containing the element must be selected.

In such a case, for example, when one wishes to compare an amino acid sequence and a base sequence which relate to completely different proteins, an increase in number of nucleic acid sequences or of amino acid sequences has so far posed nearly no problems. This is because individual sequences are sufficiently different from each other to be discriminated. Therefore, for those sequences, it has been possible to manually achieve probe selection by using a general alignment tool or blast tool. However, when one wishes to discriminate the same protein between hetero living organisms or tries to successfully discriminate similar ones such as the genus, species, and strain of a fungus body, and a polymorphic in an HLA region of a human being, operation with such a tool is dull and complicated.

Furthermore, in the case where multiple sequences serving as targets are extremely similar to each other, it is usually impossible to identify the sequences with only a mutation at one position. In many cases, the identification of the sequences cannot be performed until a set of mutations at several positions with different alignment positions is successfully extracted.

Moreover, the data amount of a database storing the sequences serving as targets has been increasing year by year, so the extraction of the above set of mutations according to a conventional method has been becoming more and more difficult.

In addition, as described in, for example, Japanese Patent Application Laid-Open No. 2003-038160, there is disclosed an algorithm which classifies the base sequences of a known biopolymer into a common region adopting the same sequence regardless of the kind of the biopolymer and a mutation region including a mutation, and designs auxiliary probes separately for the determined common region and the mutation region. However, the algorithm for designing the probes is intended for designing multiple auxiliary probes for capturing unknown genes (or DNA fragments), and is not intended for extracting a set of probes, in which similar sequences can be completely discriminated, through identification of as small a number of mutation positions as possible.

SUMMARY OF THE INVENTION

The present invention has been made in view of such a related background art, and hence an object of the present invention is to provide a method of accurately and efficiently acquiring a candidate for a set of discrimination elements for identification.

That is, according to one aspect of the present invention, there is provided a method of acquiring a set of specific elements on a specific sequence for discriminating the specific sequence from a number of sequences, including the steps of:

acquiring a group of alignment data in which each of the number of sequences is subjected to alignment processing; and acquiring a set of elements capable of discriminating the specific sequence through computational processing on the group of alignment data.

In further aspect of the acquiring method, the computational processing preferably includes the steps of:

setting a reference sequence subjected to alignment processing; and comparing an element of the reference sequence and an element of each sequence in the group of alignment data.

In further aspect of the acquiring method, the computational processing preferably has processing of, when an element of a sequence as a target and the element of the reference sequence are identical at each alignment position, removing the element of the sequence as a target.

In further aspect of the acquiring method, the computational processing preferably has processing of computing elements at multiple alignment positions having elements which are not removed after the removing processing.

In further aspect of the acquiring method, the method preferably further includes a step of evaluating the acquired set of elements.

In further aspect of the acquiring method, the computational processing is preferably a computation performed for elements on the same row of two columns arbitrarily selected from an m×n matrix $P=(b_{mn})$ in which individual sequences subjected to the alignment processing are arranged as row information and elements of individual sequences at respective alignment positions are arranged as column information.

According to another aspect of the present invention, there is provided a method of acquiring a set of specific elements on a specific sequence each of which is intended for discriminating the specific sequence from multiple sequences, including the steps of:

acquiring a group of alignment data in which each of the multiple sequences is subjected to alignment processing; and acquiring a set of elements capable of discriminating the specific sequence through computational processing on the group of alignment data.

According to another aspect of the present invention, there is provided a method of extracting a set of probes each of which is capable of specifying multiple similar base sequences, including the steps of:

acquiring a group of alignment data in which each of the multiple base sequences is subjected to alignment processing;

acquiring a set of elements capable of discriminating the specific sequence through computational processing on the group of alignment data; and evaluating elements capable of discriminating the specific sequence to acquire a set of probes capable of discriminating the specific sequence on the basis of a combination of probes which react with the specific sequence.

The present invention also encompasses a probe or a set of probes containing at least one specific element derived by using any one of the above methods.

The present invention also encompasses a probe or a set of probes composed of a partial sequence containing a specific element derived by using any one of the above methods, the partial sequence being a base sequence targeting the specific sequence, or a sequence complementary to the partial sequence.

The present invention also encompasses a probe or a set of probes containing at least one mutation element derived by using any one of the above methods, a control program to be executed by a computer for realizing the method, and a storage medium storing a control program causing a computer to execute the method.

According to another aspect of the present invention, there is provided a set of probes each of which is capable of specifying multiple similar base sequences, in which:

each of the probes is a complementary chain capable of specifically binding to a partial sequence common to at least two of the multiple base sequences; and each of the probes is constituted so as to be capable of specifying the base sequences on the basis of a combination of probes which reacted with base sequences to be specified.

The present invention makes it possible to easily acquire specific portions in similar multiple sequences through, for example, computer processing. Therefore, accurate and efficient extraction of a set of discrimination elements for identifying a specific sequence from a number of similar sequences, which has been conventionally impossible, can be performed.

Furthermore, computational processing is collectively performed on multiple pieces of sequence data subjected to alignment processing. Therefore, processing of removing positions having the same element can be easily performed. In addition, specific positions of multiple sequences can be simultaneously acquired. Therefore, a set of probe candidates capable of collectively discriminating multiple sequences can be extracted immediately through a small number of processing steps. As a result, a time period required for the processing can be shortened.

In addition, the acquired candidates are further evaluated, whereby extraction of a reduced number of sets and selection of a probe allowing identification with improved accuracy can be easily performed.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Preferred embodiments of the present invention will now be described in detail in accordance with the accompanying drawings.

Hereinafter, the present invention will be described in detail.

An embodiment of a method of extracting a set of mutation elements according to the present invention includes the steps of:

(1) acquiring a group of alignment data in which each of the number of sequences is subjected to alignment processing; and (2) acquiring a set of elements capable of discriminating the specific sequence through computational processing on the group of alignment data.

In the present invention, a group of alignment data subjected to alignment processing is acquired on the basis of data obtained after alignment processing to be described later. The group of data is preferably subjected to alignment processing in at least a common region to be compared. The term "common region" as used herein refers to a region having sequences identical to or extremely similar to each other (sequences having high homology) in a predetermined region of multiple sequences as targets, such as a common region generally used in a base sequence. In addition, the common region is preferably a region containing different positions (elements).

Figure 2:
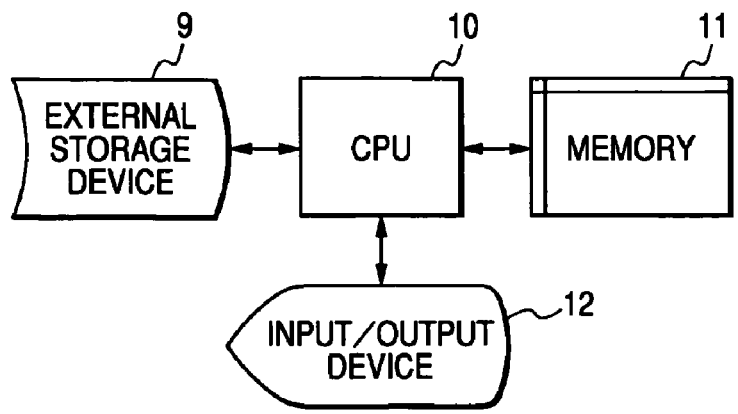
FIG. 2 is a block diagram showing a configuration of an information processing apparatus for realizing an information processing method (method of extracting elements capable of discrimination) according to the embodiment of the present invention.

FIG. 2 is a block diagram showing a configuration of an information processing apparatus for realizing an information processing method (method of extracting elements capable of discrimination) according to an embodiment of the present invention.

The extracting method according to the present invention is realized in an apparatus composed of an external storage device 9, a central processing unit (CPU) 10, a memory 11, and an input/output device 12. The external storage device 9 stores a program for realizing the extracting method according to this embodiment, and sequence data. In addition, the external storage device 9 has a function of storing a result of extraction derived by this embodiment. The central processing unit (CPU) 10 executes the program for the extracting method of the present invention or controls all the other devices. The memory 11 temporarily records the program processed by the central processing unit (CPU) 10, and a subroutine or data. The input/output device 12 performs an interaction with a user. In addition, the user inputs an execution trigger of the program via the input/output device 12. Furthermore, the user can view a result of judgment or set a parameter of the program via the input/output device 12.

A method of extracting elements capable of discrimination by using the above-mentioned system in the case where the sequence is a base sequence will be described by way of specific examples.

(1) The step of acquiring a group of alignment data in which a number of sequences are subjected to alignment processing.

First, a group of alignment data in which a number of sequences are subjected to alignment processing is acquired. Each of multiple pieces of sequence data as targets is subjected to alignment processing to acquire sequence information data in which alignment processing is performed for a common region. The range of the common region may be specified in advance. Alternatively, only the data for the common region portion may be extracted after the alignment processing has been performed.

A known technique can be directly used as an alignment method for base sequences. Software may be manufactured by oneself with reference to a literature such as "Elizabeth C. Tyler, Martha R. Horton, and Philip R. Krause 1991. A Review of Algorithms for Molecular Sequence Comparison, COMPUTERS AND BIOMEDICAL RESERACH 24:72-96". Alternatively, commercially available software such as DNASIS (Hitachi Software Engineering Co., Ltd.) and gene analysis software GENETYX (Software Development Co., Ltd.) and several kinds of multiple alignment tools which can be executed on the web such as AMAS and Box-Shade collectively introduced on Rockefeller University's website at cs.rockefeller.edu, in the subdirectory "index/php?page=toolkit-align", can be used for the present invention.

In addition, a step of sorting out multiple base sequences to be discriminated first may be provided before the alignment processing step.

The sorted multiple sequences are subjected to alignment processing by using the above-mentioned means, whereby a common region to the sequences can be represented as follows by using a matrix.

$$P = \begin{pmatrix} b_{11} & b_{12} & \cdots & \cdots & b_{1n} \\ \cdot & b_{22} & & & \cdot \\ \cdot & & b_{ii} & & \cdot \\ \cdot & & & & \cdot \\ b_{m1} & \cdots & \cdots & \cdots & b_{mn} \end{pmatrix}$$

In addition, the range of the common region may be arbitrarily set.

(Method of Defining Matrix)

P is defined as follows. A sequence composed of n bases is represented as a row vector of the character string $b_i$ (i=1, 2, 3, . . . , m), and this is defined as follows.

$b_i$=(A, T, T, T, C, G, G, T, A, A, . . . )

At this time, the respective rows correspond to the respective base sequences. That is, the following relationship is established.

$\{P \ni b_1, b_2, b_3, \ldots\}$

When a column vector $b_j$ (j=1, 2, 3, . . . , n) composed of elements of individual sequences at each alignment position j determined at this time is defined, the following relationship is established in the same manner.

$\{P \ni b_1, b_2, b_3, \ldots\}$

Individual sequence information is defined as a row, and alignment position information is defined as a column. However, the row and the column may be interchanged and the subsequent procedure may be reversed without any problem.

(Method of Extracting Element)

A specific example of the present invention will be described for the case where the number of sequences subjected to alignment is 4. As shown below, a column containing at least one element on a row different from the elements on the other rows is enclosed with □.

In this example and in the following examples, the sequence of $b_0$ corresponds to SEQ ID NO:77, the sequence of $b_1$ corresponds to SEQ ID NO:78, the sequence of $b_2$ corresponds to SEQ ID NO:79, the sequence of $b_3$ corresponds to SEQ ID NO: 80, and the sequence of $b_4$ corresponds to SEQ ID NO:81.

$$P = \begin{bmatrix} b_1 \\ b_2 \\ b_3 \\ b_4 \end{bmatrix} = \begin{bmatrix} T\,A\,\boxed{C}\,C\,T\,G\,G\,A\,C\,A\,G\,A\,T\,\boxed{A}\,C\,T\,T\,C\,C\,A\,T\,\boxed{G}\,A\,C \\ T\,A\,\boxed{C}\,C\,T\,G\,G\,A\,C\,A\,G\,A\,T\,\boxed{C}\,C\,T\,T\,C\,C\,A\,T\,\boxed{A}\,A\,C \\ T\,A\,\boxed{C}\,C\,T\,G\,G\,A\,C\,A\,G\,A\,T\,\boxed{C}\,C\,T\,T\,C\,C\,A\,T\,\boxed{A}\,A\,C \\ T\,A\,\boxed{G}\,C\,T\,G\,G\,A\,C\,A\,G\,A\,T\,\boxed{A}\,C\,T\,T\,C\,C\,A\,T\,\boxed{G}\,A\,C \end{bmatrix}$$

Alignment position: 1 2 3 4 5 6 7 8 9 10 11 12 13 14 15 16 17 18 19 20 21 22 23 24

As can be seen from the above, no mutation elements are present on the other portions, so a predetermined computation causes no change. Therefore, it is sufficient that the subsequent computation be performed for a column enclosed with □. As a result, computational processing can be simplified.

Next, only the extracted columns each enclosed with □ are subjected to computational processing.

A desirable example of the predetermined computation is as follows. The sequence on the $b_1$ row is selected as a sequence as a computation target. Then, computational results are obtained according to the defined computation from the column vector at the alignment position 22 sequentially in the left direction.

(More Specific Computation Method)

The computation method described above will be described more specifically. In this embodiment, "processing of discriminating and removing different elements" is performed.

The "processing of discriminating and removing different elements" is processing in which, at an alignment position as a target, the sequence to be compared is set as an element on the $b_1$ row, and the sequences on the $b_2$, $b_3$, and $b_4$ rows are discriminated and removed. The procedure is as follows.

$$\begin{pmatrix} G \\ A \\ A \\ G \end{pmatrix} \Rightarrow \begin{pmatrix} G \\ - \\ - \\ G \end{pmatrix} \quad (1)$$

$$\begin{pmatrix} A \\ C \\ C \\ A \end{pmatrix} \Rightarrow \begin{pmatrix} A \\ - \\ - \\ A \end{pmatrix} \quad (2)$$

$$\begin{pmatrix} C \\ C \\ C \\ G \end{pmatrix} \Rightarrow \begin{pmatrix} C \\ C \\ C \\ - \end{pmatrix} \quad (3)$$

Here, the eliminated elements are represented by using a symbol -. The kind of symbol is not limited. Here, the elements different from the element on the $b_1$ row (G in (1), A in (2), and C in (3)) are discriminated through the computation.

The column vectors obtained as a result of the above computation are subjected to computational processing together with the other different column vectors to further remove "different elements".

In the computational processing in this case, it is assumed that two elements on the respective rows of two column vectors are not removed only when they do not correspond to the targets of removal (none of them is -). The computation is represented as follows by using a symbol @.

$$\begin{pmatrix} G \\ - \\ - \\ G \end{pmatrix} @ \begin{pmatrix} A \\ - \\ - \\ A \end{pmatrix} = \begin{pmatrix} A \\ - \\ - \\ A \end{pmatrix} \quad (4)$$

$$\begin{pmatrix} A \\ - \\ - \\ A \end{pmatrix} @ \begin{pmatrix} C \\ C \\ C \\ - \end{pmatrix} = \begin{pmatrix} C \\ - \\ - \\ - \end{pmatrix} \quad (5)$$

The computational results on the right sides of the equation (4) and the equation (5) simply represent whether elements on the respective columns survive. In this example, substitution is performed by using an element on the second term of the left side. However, intrinsically, any kind of symbol may be used.

Then, the column vectors with their different elements discriminated and removed through comparison with the $b_1$ row, that is, the column 22, the column 14, and the column 3 are sequentially selected and subjected to the computation @ from the equation (4) to the equation (5). As a result, the computational result reaches the minimum value of 1 indicating that only one element remains.

The value 1 means that extracting a set of mutation elements for identification succeeded, that is, no sequence identical to ($b_1$) is present and the sequence $b_1$ can be separated and identified from any other sequences by using the set of mutation elements. In addition, the number of candidates changes in such a manner as 2 (processing result of the equation (1))→
2 (processing result of the equation (4))→
1 (processing result of the equation (5))

during a period in which the initial value at the start of computation reaches the minimum value. The columns in each of which the number of candidates can be reduced are the column 22 and the column 3 when the initial value is included. Therefore, the set of mutation elements are G on the column 22 and C on the column 3, that is, the underlined portions in the following equation.

$b_{1\text{-}set}$=(TAC̲CTGGACAGATACTTCCATG̲AC)

Next, the discriminating and removing processing is performed on the basis of the sequence on the $b_2$ row. When the computation @ is performed in the same manner as that described above, the minimum value is not 1 but 2 as follows.

$$\begin{pmatrix} - \\ A \\ A \\ - \end{pmatrix} @ \begin{pmatrix} - \\ C \\ C \\ - \end{pmatrix} = \begin{pmatrix} - \\ C \\ C \\ - \end{pmatrix} \quad (6)$$

$$\begin{pmatrix} - \\ C \\ C \\ - \end{pmatrix} @ \begin{pmatrix} C \\ C \\ C \\ - \end{pmatrix} = \begin{pmatrix} - \\ C \\ C \\ - \end{pmatrix} \quad (7)$$

In view of the above, the rows in which elements survive are collected and compared.

$b_{2\text{-}set}$=(TACCTGGACAGATCCTTCCATA̲AC)

$b_{3\text{-}set}$=(TACCTGGACAGATCCTTCCATA̲AC)

As a result of comparison, it can be judged that the $b_2$ and $b_3$ regions have no elements with which the regions can be discriminated from each other. They may be compared with each other on a programming language by using a character-string comparison function or through logical comparison on a character basis. The element A on the column 22 selected as the initial value by the first computation indicates that it can be discriminated from at least $b_1$ and $b_4$ and is not useless.

Furthermore, the computation @ is performed for the $b_4$ row, whereby the following results are obtained.

$$\begin{pmatrix} G \\ - \\ - \\ G \end{pmatrix} @ \begin{pmatrix} A \\ - \\ - \\ A \end{pmatrix} = \begin{pmatrix} A \\ - \\ - \\ A \end{pmatrix} \quad (8)$$

$$\begin{pmatrix} A \\ - \\ - \\ A \end{pmatrix} @ \begin{pmatrix} - \\ - \\ - \\ G \end{pmatrix} = \begin{pmatrix} - \\ - \\ - \\ G \end{pmatrix} \quad (9)$$

$b_{4\text{-}set}$=(TAG̲CTGGACAGATACTTCCATGAC) (10)

On the other hand, if the column on the most left side containing a mutation element is set at a start column and computations are sequentially performed for the columns which are not discriminated or removed in the right direction, the result to be obtained is as follows.

$b_{4\text{-}set}$=(TAG̲CTGGACAGATACTTCCATGAC) (11)

Therefore, the set of mutation elements can be represented by using a reduced number of elements.

That is, the above computational processing resulted in obtaining the set of mutation elements capable of discriminating all the four kinds of sequences (in actuality, three kinds because $b_2$ and $b_3$ are the same). The processing is characterized in that specific portions in the respective sequences are collectively extracted, thereby eliminating operation of sorting probes for individual sequences.

It should be noted that $b_{1\text{-}set}$ to $b_{4\text{-}set}$ can be discriminated from each other even when the computation is performed in the right direction because they are represented as follows.

$b_{1\text{-}set}$ = (TACCTGGACAGATACTTCCATGAC)

$b_{2\text{-}set}$ = (TACCTGGACAGATCCTTCCATAAC)

$b_{3\text{-}set}$ = (TACCTGGACAGATCCTTCCATAAC)

$b_{4\text{-}set}$ = (TAGCTGGACAGATACTTCCATGAC)

That is, the embodiments of the computation (and the evaluation) may be in the right direction or the left direction. In addition, the computation may not be performed for adjacent elements sequentially and the computation may not be performed from an end. For example, an algorithm may be devised in such a manner that the number of elements for one computational result reaches the minimum value of 1 while incessantly selecting a value to be minimum.

More simply, for example, a column vector may be selected in such a manner that only the initial value of the number of elements becomes minimum, and then a computation may be simply performed for the column vector in the right or left direction.

With using such a scheme, the sequence can be characterized by using as small a number of sets of mutation elements as possible. This is preferable because the number of probes to be arranged can be minimized when the probes are used as probes for DNA chips.

In contrast, if such a scheme is not used, the number of sets of mutation elements relatively increases, so that the following features are obtained:

i) the sets are relatively robust under various conditions of an assay;

ii) it may be possible to collect the sets of mutation elements within a relatively narrow range when a computation is sequentially performed; and iii) when the assay is a quantitative PCR method, a large number of mutation elements are easily collected on an upstream side if the computation is performed in the 3'→5' direction (left direction in the example) (it is advantageous in program coding). Therefore, such a scheme is preferably used if required.

A sample prepared from a genome contains an extremely large number of similar sequences. From such a point of view, reducing the number of mutation elements has advantages and disadvantages. Therefore, any method can be adopted for the embodiment of the present invention.

(Another Embodiment of Computational Processing)

In addition, the "processing of discriminating and removing different elements" may adopt the following form. When a $b_0$ row is added to the matrix P, and discrimination and removal are performed against $b_0$, the following result is obtained.

$$P = \begin{bmatrix} b_0 \\ b_1 \\ b_2 \\ b_3 \\ b_4 \end{bmatrix} = \begin{bmatrix} \text{T T G C T G G A C A G A T G C A T C C A T A A C} \\ \text{- A C - - - - - - - - - - A - T - - - - - G - -} \\ \text{- A C - - - - - - - - - - C - T - - - - - - - -} \\ \text{- A C - - - - - - - - - - C - T - - - - - - - -} \\ \text{- A - - - - - - - - - - - A - T - - - - - G - -} \end{bmatrix}$$

Alignment position: 1 2 3 4 5 6 7 8 9 0 1 2 3 4 5 6 7 8 9 0 1 2 3 4

Then, attention is paid to a small matrix of P obtained by removing the $b_0$ row. Since the computation @ provides the same results as those described above for $b_1$, $b_2$, and $b_3$, the computation is performed for surviving elements in $b_4$.

$$\begin{pmatrix} G \\ - \\ - \\ G \end{pmatrix} @ \begin{pmatrix} T \\ T \\ T \\ T \end{pmatrix} = \begin{pmatrix} T \\ - \\ - \\ T \end{pmatrix} \quad (12)$$

-continued $$\begin{pmatrix} T \\ - \\ - \\ T \end{pmatrix} @ \begin{pmatrix} A \\ C \\ C \\ A \end{pmatrix} = \begin{pmatrix} A \\ - \\ - \\ A \end{pmatrix} \quad (13)$$

$$\begin{pmatrix} A \\ - \\ - \\ A \end{pmatrix} @ \begin{pmatrix} A \\ A \\ A \\ A \end{pmatrix} = \begin{pmatrix} A \\ - \\ - \\ A \end{pmatrix} \quad (14)$$

Rows in which elements survive are collected and compared.

$$b_{1\text{-}set} = (\text{-AC- - - - - - - - - - A-T - - - - -G- -})$$

$$b_{4\text{-}set} = (\text{-A- - - - - - - - - - - A-T - - - - -G- -})$$

Since the rows are different, a set of mutation elements for identification of $b_4$ exists and is G on the column 22. In the above result of 10 and 11, G on the column 22 may be present or absent, and G on the column 3 was an essential identification element. However, in this case, G on the column 22 is an essential identification element. The presence of G on the column 3 in the newly added bo serves as a background for this.

Therefore, it is understood that the present invention is valid even in such "processing of discriminating and removing different elements".

It is possible to extract a set of mutation elements from the added bo. It can be extracted in exactly the same manner as that described above by using the computation @. This is because the "processing of discriminating and removing different elements" (i.e., symbol discrimination) is merely a problem of forward and reverse occurring in a logical proposition. Therefore, the matrix P can be rewritten as follows.

$$P = \begin{bmatrix} b_0 \\ b_1 \\ b_2 \\ b_3 \\ b_4 \end{bmatrix} = \begin{bmatrix} \text{- T G - - - - - - - - - - G - A - - - - - A - -} \\ \text{- - - - - - - - - - - - - - - - - - - - - - - -} \\ \text{- - - - - - - - - - - - - - - - - - - - - - A - -} \\ \text{- - - - - - - - - - - - - - - - - - - - - - A - -} \\ \text{- - G - - - - - - - - - - - - - - - - - - - - -} \end{bmatrix} \quad (18)$$

Alignment position: 1 2 3 4 5 6 7 8 9 0 1 2 3 4 5 6 7 8 9 0 1 2 3 4

Then, it is sufficient that the above-mentioned "computation @" be performed. In this case, without the computation it is readily understood that T, G, and A on the column 2, the column 14, and the column 16 are independently a set of mutation elements for identification of $b_0$.

(Another Embodiment of Computation Method)

A base sequence having the simplest four notations A, C, T, and G has been described as a sequence. However, the present invention is not limited to this. Extraction can also be performed for a simple list of characters. For example, as is often the case, one symbol * indicating deficiency of a base may be added to the matrix P (see below).

$$P = \begin{bmatrix} b_1 \\ b_2 \\ b_3 \\ b_4 \end{bmatrix} = \begin{bmatrix} \text{Alignment position:} & 1\ 2\ 3\ 4\ 5\ 6\ 7\ 8\ 9\ 1\ 1\ 2\ 3\ 4\ 5\ 6\ 7\ 8\ 9\ 2\ 0\ 2\ 3\ 4 \\ T\ A\ \boxed{C}\ C\ T\ G\ G\ A\ C\ A\ G\ A\ T\ \boxed{A}\ C\ T\ T\ C\ C\ A\ T\ \boxed{G}\ A\ C \\ T\ A\ \boxed{C}\ C\ T\ G\ G\ A\ C\ A\ G\ A\ T\ \boxed{*}\ C\ T\ T\ C\ C\ A\ T\ \boxed{A}\ A\ C \\ T\ A\ \boxed{C}\ C\ T\ G\ G\ A\ C\ A\ G\ A\ T\ \boxed{C}\ C\ T\ T\ C\ C\ A\ T\ \boxed{A}\ A\ C \\ T\ A\ \boxed{G}\ C\ T\ G\ G\ A\ C\ A\ G\ A\ T\ \boxed{A}\ C\ T\ T\ C\ C\ A\ T\ \boxed{G}\ A\ C \end{bmatrix}$$

When the symbol * is treated in the same manner as in A, C, T, and G, $b_2$ and $b_3$ can be discriminated according to the same computation as that described above, and it is apparent that the following equation is established.

$$b_{2\text{-}set} = (\text{TACCTGGACAGAT*CTTCCATAAC})$$

As seen from the above, a base sequence containing a deletion, substitution or insertion may be expressed as a mutation sequence having a mutation point represented by a specific symbol.

In addition, in the case where one symbol is added, for example, a completely meaningless symbol may be added. In the following P, a symbol | represents an exon boundary. At this time, the symbol | does not become a different element even when the symbol is placed in any row, and hence has no computational meaning. However, in the case of a genome sample, it is impossible to select a sequence across the exon boundary as a probe, so that the symbol provides probe design software with significant information.

$$P = \begin{pmatrix} b_1 \\ b_2 \\ b_3 \\ b_4 \end{pmatrix} = \begin{pmatrix} T & A & \boxed{C} & C & T & G & G & A & C & A & G & | & A & T & \boxed{A} & C & T & T & C & C & A & T & \boxed{G} & A & C \\ T & A & \boxed{C} & C & T & G & G & A & C & A & G & | & A & T & \boxed{*} & C & T & T & C & C & A & T & \boxed{A} & A & C \\ T & A & \boxed{C} & C & T & G & G & A & C & A & G & | & A & T & \boxed{C} & C & T & T & C & C & A & T & \boxed{A} & A & C \\ T & A & \boxed{G} & C & T & G & G & A & C & A & G & | & A & T & \boxed{A} & C & T & T & C & C & A & T & \boxed{G} & A & C \end{pmatrix}$$

That is, the computation defined in the present invention does not depend on the kinds and number of symbols. Neither of amino acid one character notation represented by using an increased number of symbols, that is, 20 symbols nor IUB (International Union of Biochemistry) notation of a base sequence poses problems.

(Evaluation of Computational Result)

In the present invention, it is desirable that a step for evaluating an obtained discrimination element be provided.

For example, when a hybridization probe is selected from the obtained discrimination elements, a probe having a Tm value considerably different from others can be obtained by setting as a probe a sequence in which a deficient portion is placed at a central portion and from which a deficiency symbol is removed.

In actuality, a set of mutation elements for identification thus extracted provides information necessary for hybridization on a DNA microarray or for probe selection of the quantitative PCR method. In the case of hybridization, if a sequence of about 20 bases (in the case of detection of one base mismatch) is cut out in such a manner that the mutation element for identification is placed at substantially the central portion of the probe, a large difference in Tm value between full match and mismatch tends to occur. In this case, separation and identification are easily performed by successfully setting a reaction temperature at a boundary between the full match and the mismatch. In the case of the quantitative PCR method, if the sequence of about 20 bases is cut out in such a manner that the mutation element for identification is placed on the 3' terminal side in order to prevent heat-resistant polymerase from extending a chain, separation and identification are easily performed.

It is needless to say that, in each of the methods, when a probe has as large a number of mismatches as possible, the probe can be easily separated and identified.

That is, in determining the set of mutation elements, the number of mismatches in a probe is restricted or the presence of mutation of an amino acid level is set as a condition for a probe candidate (or set of mutation elements), whereby it becomes possible to perform the "predetermined evaluation" defined in the present invention.

In this embodiment, with the aim of extracting multiple surviving elements (elements which are not removed) through a computation and reducing the number of candidates when the multiple elements are defined as candidates, the other columns are sequentially selected and subjected to a computation.

The computation at this time is such that the preceding computational result is logically multiplied by the computational result of the column vector to be selected next. That is, the computation is such that the number of candidates can be reduced with only a logical product.

(Another Embodiment of Evaluation of Computational Result)

In this embodiment, as an evaluation step for reducing the number of candidates with improved efficiency, evaluation is performed in consideration of a partial sum.

In the following example, over the columns 16 to 18, GAT (Asp) is mutated to AGC (Ser). In addition, for viewability, each row vector is collectively noted on a codon basis.

$$P = \begin{pmatrix} b_1 \\ b_2 \\ b_3 \\ b_4 \end{pmatrix} = \begin{pmatrix} GAG & CTG & GG\boxed{G} & CGG & CCT & \boxed{GAT} & GCC & GAG & TAC & TGG \\ GAG & CTG & GG\boxed{C} & CGG & CCT & AGC & GCC & GAG & TAC & TGG \\ GAG & CTG & GG\boxed{A} & CGG & CCT & AGC & GCC & GAG & TAC & TGG \\ GAG & CTG & GG\boxed{G} & CGG & CCT & \boxed{AGC} & GCC & GAG & TAC & TGG \end{pmatrix}$$

Alignment Position: 1 2 3  4 5 6  7 8 9  0 1 2  3 4 5  6 7 8  9 0 1  2 3 4  5 6 7  8 9 0

When one wishes to set mutation of an amino acid level as an evaluation condition, a set of mutation elements is determined if a vector is represented again with an amino acid one character code and a computation is performed (However, in the example, $b_2$, $b_3$, and $b_4$ cannot be discriminated. One base mutation on the column 9 does not suffice for the change of an amino acid.).

In addition, with only the logical product (process of multiplying the preceding computational result by the computational result of the column vector to be selected next) described above, elements on the column 18 are selected in $b_2$, $b_3$, and $b_4$, and the number of candidates cannot be reduced in each of the column 17 and the column 16. Therefore, the columns 16 and 17 do not remain as candidates. However, when a logical sum (process of independently computing a column and another column, instead of multiplying the preceding computational result by the computational result of the column vector to be selected next) is taken into consideration, it is understood that, in $b_2$, the computational results of the column 16, the column 17, and the column 18 are equivalent to one another (the columns have the same number of remaining elements and the same row positions of the remaining elements) as follows.

$$\begin{bmatrix} - \\ C \\ C \\ C \end{bmatrix} @ \begin{bmatrix} - \\ C \\ - \\ - \end{bmatrix} \begin{bmatrix} - \\ C \\ - \\ - \end{bmatrix} \quad (15)$$
Column 18

$$\begin{bmatrix} - \\ G \\ G \\ G \end{bmatrix} @ \begin{bmatrix} - \\ C \\ - \\ - \end{bmatrix} \begin{bmatrix} - \\ C \\ - \\ - \end{bmatrix} \quad (16)$$
Column 17

$$\begin{bmatrix} - \\ A \\ A \\ A \end{bmatrix} @ \begin{bmatrix} - \\ C \\ - \\ - \end{bmatrix} \begin{bmatrix} - \\ C \\ - \\ - \end{bmatrix} \quad (17)$$
Column 16

In this case, mutation of an amino acid level can be extracted if an evaluation condition that "if the computational results of adjacent columns are equivalent three consecutive times, the columns are left as candidates" is provided.

In addition, similarly, when an evaluation condition that "containing two mutations within consecutive 20 mer" is provided, in $b_3$, for example, the following is established.

$b_{3\text{-}set}$=(GAG CTG GGA CGG CCT AGC GCC GAG TAC TGG)(computation in the right direction)

Setting an evaluation condition as described above in such a manner that a more excellent probe for separation and identification is obtained poses no problems. If the number of elements does not finally become 1 depending on an evaluation condition, a recursive algorithm may be prepared in such a manner that conditions are sequentially relaxed and then the number of elements reaches 1.

In addition, the form of the present invention as shown in the equation (18) is convenient for simulating difference in assay results depending on samples in the case where a sample to be actually subjected to hybridization is a mixture of multiple similar sequences.

For example, as an actual case, the following operation is not easy: a DNA microarray for separating and identifying a DRB allergen in an MHC region of a human being is designed and whether each probe in the designed array is problematic or not is confirmed through hybridization using an actual sample. At present, nearly 400 kinds of DRB alleles have been reported, and a sample is present as a mixture of paternal and maternal DNAs.

In addition, in an unfortunate case, a sample after the PCR may be a mixture of 4 kinds containing DRB1 and DRB3. If it is assumed that the sample is a mixture of two kinds out of 100 alleles, the number of combinations for the mixture is $_{100}C_2$=4,950. Therefore, it is very hard to evaluate the performance of all samples with an actual sample.

However, the form as shown in the equation (18) automatically adds important information because the set of mutation elements is represented as follows.

$b_{1\text{-}set}$=(-AC---------A-T-----G--)

Suppose that one containing a mismatch at a terminal thereof is selected as a probe for quantitative PCR in such a manner that Tm does not exceed 53° C. When comparison is performed with reference to the sequence of $b_0$ and the - symbol is substituted by a base, a lowercase character is used. Thus, the following is established.

$b_{0\text{-}part}$=(TGGACAGATGCATCCATA)

$b_{1\text{-}part}$=(---------A-T-----G) and hence $b_{1\text{-}prob}$=(tggacagatAcTtccatG)(Tm calculation is according to Wallac method)

Here, uppercase characters A and T in $b_{1\text{-}prob}$ are mismatches viewed from $b_0$, but are not sets of elements for discriminating mutation. However, $b_{1\text{-}prob}$ itself contains a total of three mismatches, and it is understood that the probe is not very bad as compared to a probe containing one mismatch. Furthermore, $b_0$ is changed and, for example, four kinds of possible alleles in a sample are similarly investigated. Furthermore, in various possible samples, investigations can be easily performed with reference to computational results as to which allergen is hardly separated and identified owing to which probe in which sample.

In addition, in the above description, a partial base sequence containing a specific base sequence obtained as a result of computation has been generated as a probe. However, a base sequence complementary to the partial base sequence may be provided as a probe.

While a set of sequence information concerning a number of sequences as a target is respectively acquired before alignment processing in the above, such an entire set of consecutive sequence information may not necessarily be obtained previously. Instead, known alignment data containing only mutation points of a number of specific sequences may be arranged in order.

In that case, the step of removing the elements at an alignment position where they are identical can be omitted. That is, the step of acquiring a group of alignment data can be replaced by a step of acquiring reference sequence data subjected to alignment processing and mutation element data of each sequence from the reference sequence for implementing the present invention.

Example

Figure 1:
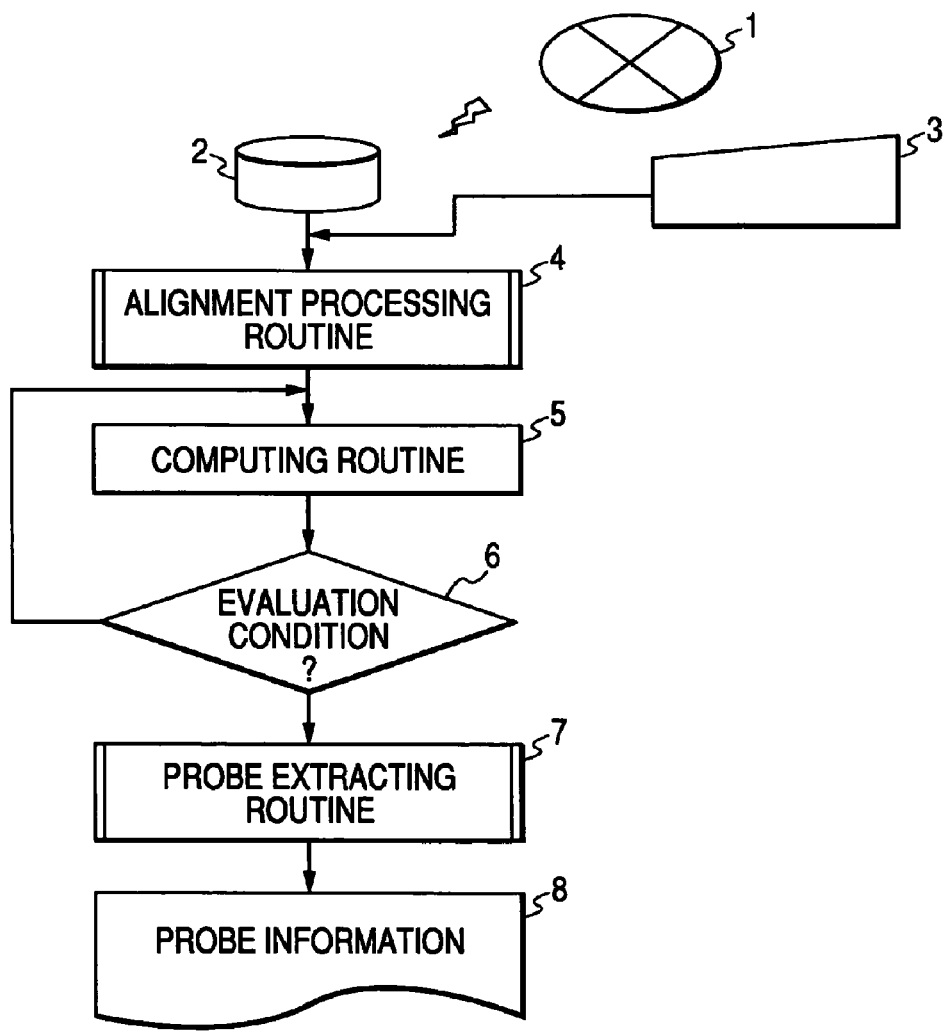
FIG. 1 is a flow chart showing an embodiment of the present invention.

A system for specifically carrying out the above-mentioned method will be described in more detail. The flow shown in FIG. 1 represents an embodiment of the present invention. A database of gene information sequence is present on a network drive 2 through an internet 1 (or is originally present).

Selection of multiple sequences is performed by an operator who operates a keyboard 3.

The selected multiple sequences are subjected to alignment on an alignment processing routine 4. After the alignment, a range (common region after the alignment) for searching a set of mutation elements for identification is defined on the basis of information inputted through the keyboard 3 by the operator, and is subjected to a computation by a computing routine 5. At this time, evaluation is performed on the basis of an evaluation condition 6 of computation (which may be similarly given from the operator or may be programmed in advance), and the computation is trial until a predetermined result (minimum value) is achieved. A probe extracting routine 7 determines a probe for an element surviving after the trial (passing the evaluation condition) on the basis of information inputted through the keyboard 3 by the operator, and the determined probe information 8 is outputted.

Next, a specific example of extraction of a set of mutation elements or a set of probes for separation and identification of an allele in DRB of MHC of a human being will be given. A group of alleles selected from the database are approved alleles frequently seen in the Japanese, and a family P thereof is represented as follows.

P = { DRB1*010101 DRB1*010102 DRB1*030101 DRB1*030102 DRB1*040101
DRB1*040102 DRB1*040301 DRB1*040302 DRB1*0404 DRB1*040501
DRB1*040502 DRB1*040503 DRB1*040504 DRB1*0406 DRB1*040701
DRB1*040702 DRB1*0410 DRB1*070101 DRB1*070102 DRB1*080201
DRB1*080202 DRB1*080203 DRB1*080302 DRB1*0809 DRB1*090102
DRB1*100101 DRB1*100102 DRB1*110101 DRB1*110102 DRB1*110103
DRB1*110104 DRB1*120101 DRB1*120102 DRB1*120201 DRB1*120202
DRB1*130101 DRB1*130102 DRB1*130103 DRB1*130201 DRB1*130202
DRB1*130701 DRB1*130702 DRB1*140101 DRB1*140102 DRB1*1402
DRB1*1403 DRB1*140501 DRB1*140502 DRB1*1406 DRB1*140701
DRB1*140702 DRB1*1412 DRB1*1429 DRB1*150101 DRB1*150102
DRB1*150103 DRB1*150104 DRB1*150201 DRB1*150202 DRB1*150203
DRB1*160201 DRB1*160202 DRB3*010101 DRB3*01010201 DRB3*01010202
DRB3*010103 DRB3*010104 DRB3*020201 DRB3*020202 DRB3*020203
DRB3*020204 DRB3*030101 DRB3*030102 DRB4*0102 DRB4*01030101
DRB4*010302 DRB4*010303 DRB4*010304 DRB5*010101 DRB5*010102
DRB5*0102 DRB5*0202}

Conditions for carrying out the processing method were:
i) a range for searching a set of mutation elements for identification should be 113 to 345 of exon 2;
ii) a probe should have a mutation element on its 3' terminal;
iii) the probe of ii) should have Tm not exceeding 55° C.; and
iv) mutation corresponding to DRB1*010101 should be represented by using an uppercase character. Next, outputted results are shown.

(Outputted Results)
Result of PROBE EXTRACTOR programmed by Tsukada Mamoru, Canon Inc., Japan.
This is Program to investigate and to discriminate Allel Sequence in which includes SNPs.
Set of oligonucleotide sequences can prove that the allele is Unique by this set.
note) Each probe has direction 5' to 3', and is designed for using Real Time PCR method.
Capital letter indicates position of SNPs viewing from DRB1*010101.
If next number from allele name is '1', indicates that the allele is Unique by this set.
The sequences of reference numbers 0 to 75 correspond to SEQ ID NOs. 1 to 76.

| OUTPUT FILE: search from 113 to 345 | | | | | | |
|---|---|---|---|---|---|---|
| DRB1*010101 | 1 | 0 | 1 | 2 | 3 | 4 5 |
| DRB1*010102 | 1 | 6 | | | | |
| DRB1*030101 | 1 | 7 | 8 | | | |
| DRB1*030102 | 1 | 7 | 9 | 8 | | |
| DRB1*040101 | 1 | 10 | 11 | | | |
| DRB1*040102 | 1 | 12 | | | | |
| DRB1*040301 | 1 | 10 | 13 | 14 | 8 | |
| DRB1*040302 | 1 | 10 | 15 | 14 | 8 | |
| DRB1*0404 | 1 | 10 | 13 | 8 | | |
| DRB1*040501 | 3 | 10 | 16 | | | |
| DRB1*040502 | 1 | 17 | | | | |
| DRB1*040503 | 3 | 10 | 16 | | | |

-continued

| OUTPUT FILE: search from 113 to 345 | | | | | |
|---|---|---|---|---|---|
| DRB1*040504 | 3 | 10 | 16 | | |
| DRB1*0406 | 1 | 10 | 14 | 8 | |
| DRB1*040701 | 1 | 10 | 13 | 14 | |
| DRB1*040702 | 1 | 18 | | | |
| DRB1*0410 | 1 | 16 | 8 | | |
| DRB1*070101 | 1 | 19 | | | |
| DRB1*070102 | 1 | 20 | 19 | | |
| DRB1*080201 | 2 | 21 | 22 | 23 | |
| DRB1*080202 | 2 | 21 | 22 | 23 | |
| DRB1*080203 | 1 | 24 | | | |
| DRB1*080302 | 1 | 16 | 23 | | |
| DRB1*0809 | 1 | 25 | 22 | 23 | |
| DRB1*090102 | 1 | 26 | | | |
| DRB1*100101 | 1 | 27 | | | |
| DRB1*100102 | 1 | 28 | 29 | | |
| DRB1*110101 | 2 | 30 | | | |
| DRB1*110102 | 2 | 30 | | | |
| DRB1*110103 | 1 | 30 | 31 | | |
| DRB1*110104 | 1 | 32 | 30 | | |
| DRB1*120101 | 1 | 33 | 34 | 35 | |
| DRB1*120102 | 1 | 33 | 34 | | |
| DRB1*120201 | 1 | 33 | 22 | 35 | |
| DRB1*120202 | 1 | 33 | 22 | 31 | |
| DRB1*130101 | 1 | 36 | 37 | 8 | |
| DRB1*130102 | 1 | 38 | | | |
| DRB1*130103 | 1 | 37 | 35 | 8 | |
| DRB1*130201 | 1 | 36 | 37 | | |
| DRB1*130202 | 1 | 37 | 39 | | |
| DRB1*130701 | 1 | 40 | 41 | 21 | 22 | 42 |
| DRB1*130702 | 1 | 41 | 15 | 22 | 42 |
| DRB1*140101 | 1 | 43 | 44 | 8 | |
| DRB1*140102 | 1 | 43 | 8 | | |
| DRB1*1402 | 1 | 45 | 46 | 47 | 48 |
| DRB1*1403 | 1 | 45 | 48 | 49 | 23 |
| DRB1*140501 | 1 | 50 | 51 | | |
| DRB1*140502 | 1 | 50 | | | |
| DRB1*1406 | 1 | 45 | 46 | 47 | 48 | 8 |
| DRB1*140701 | 2 | 43 | 44 | | |
| DRB1*140702 | 2 | 43 | 44 | | |
| DRB1*1412 | 1 | 23 | 8 | | |
| DRB1*1429 | 1 | 47 | 49 | 52 | |
| DRB1*150101 | 1 | 53 | 15 | 54 | 8 |
| DRB1*150102 | 1 | 55 | 56 | | |
| DRB1*150103 | 1 | 54 | 35 | 8 | |
| DRB1*150104 | 1 | 53 | 54 | 8 | |
| DRB1*150201 | 1 | 53 | 15 | 54 | |
| DRB1*150202 | 1 | 53 | 54 | | |
| DRB1*150203 | 1 | 57 | | | |
| DRB1*160201 | 1 | 58 | 31 | | |
| DRB1*160202 | 1 | 58 | 59 | | |
| DRB3*010101 | 3 | 60 | 61 | 7 | 9 |
| DRB3*01010201 | 3 | 60 | 61 | 7 | 9 |
| DRB3*01010202 | 3 | 60 | 61 | 7 | 9 |
| DRB3*010103 | 1 | 62 | 7 | 9 | |
| DRB3*010104 | 1 | 9 | 55 | | |
| DRB3*020201 | 1 | 63 | 64 | | |
| DRB3*020202 | 1 | 63 | | | |
| DRB3*020203 | 1 | 65 | | | |
| DRB3*020204 | 1 | 63 | 66 | 64 | |
| DRB3*030101 | 1 | 67 | 64 | 8 | |
| DRB3*030102 | 1 | 68 | | | |
| DRB4*0102 | 1 | 69 | | | |
| DRB4*01030101 | 2 | 70 | | | |
| DRB4*010302 | 2 | 70 | | | |
| DRB4*010303 | 1 | 70 | 44 | | |
| DRB4*010304 | 1 | 71 | | | |
| DRB5*010101 | 1 | 72 | 31 | | |
| DRB5*010102 | 1 | 72 | | | |
| DRB5*0102 | 1 | 73 | 74 | 31 | |
| DRB5*0202 | 1 | 73 | 75 | | |

| 0 | atc tat aac caa gag gag TC |
|---|---|
| 1 | g ctg ggg cgg cct gaT |
| 2 | g ggg cgg cct gaT gcC |
| 3 | gg aac agc cag aag gac C |
| 4 | gac Ctc ctg gag cag AG |
| 5 | cac aac tac ggg gTt gGT |
| 6 | gc atc tat aac caa gag gaA |
| 7 | ag cag aAg cgg gGc CG |
| 8 | cac aac tac ggg gtt gTG |
| 9 | gg gGc CGg gtg gac aAT |
| 10 | C ctg gaC aga tAc Ttc tat C |
| 11 | g gac ctc ctg gag cag aA |
| 12 | aga tAc Ttc tat Cac caa gaA |
| 13 | Ttc tat Cac caa gag gag tA |
| 14 | ag cag agg cgg gcc gA |
| 15 | g ggg cgg cct gaC gcT |
| 16 | ag ctg ggg cgg cct AG |
| 17 | caa gag gag tAc gtg cgG |
| 18 | gac ctc ctg gag cag agA |
| 19 | gg gcg gtg acg gag ctA |
| 20 | t ttc Ctg tgg cag GGt aaA |
| 21 | c Ttc tat aac caa gag gag tA |
| 22 | gg aac agc cag aag gac T |
| 23 | gaA GaC agg cgg gcc CT |
| 24 | ag tac cgg gcg gtg acA |
| 25 | tc Cat aac caG gag gag tT |
| 26 | cg gag cgg gtg cgg tAT |
| 27 | c ctg gag cGg agg cgT |
| 28 | gg ttg ctg gaa aga Cgc G |
| 29 | c ctg gag cGg agg cgC |
| 30 | ctg ggg cgg cct gat gA |
| 31 | tc ctg gaA GaC agg cgC |
| 32 | Ct gaG tgt cat ttc ttc aaC |
| 33 | tc Cat aac caG gag gag C |
| 34 | gg aac agc cag aag gac A |
| 35 | cc gcg gtg gac acc taT |
| 36 | ag gac Atc ctg gaA GaC G |
| 37 | g gac Atc ctg gaA GaC GA |
| 38 | tg gaA GaC GAg cgg gcT |
| 39 | tc ctg gaA GaC GAg cgC |
| 40 | tc ttg GAg TaC TCt aCg tC |

-continued

| | |
|---|---|
| 41 | cgg ttC ctg gaC aga tAc T |
| 42 | g aag gac Ttc ctg gaA GaC |
| 43 | cgg cct gCt gcG gag C |
| 44 | gcc gAg gtg gac acc taT |
| 45 | cgt ttc ttg GAg TaC TCt aC |
| 46 | gg gtg cgg ttC ctg gaG |
| 47 | aG aga tAc Ttc Cat aac caG |
| 48 | Ttc Cat aac caG gag gag A |
| 49 | tc Cat aac caG gag gag AA |
| 50 | C TCt aCg tCt gaG tgt caA |
| 51 | g ggg cgg cct gat gcT |
| 52 | c aga cac aac tac ggg gC |
| 53 | agc gac gtg ggg gag tT |
| 54 | gac Atc ctg gag cag GC |
| 55 | c tgc aga cac aac tac ggA |
| 56 | a cac aac tac ggA gtt gTG |
| 57 | ctg gaC aga tAc Ttc tat saT |
| 58 | Ctg tgg cag cCt aag AGG |
| 59 | aag gac ctc ctg gaA GaC |
| 60 | g ctg ggg cgg cct gTC |
| 61 | gg cct gTC gcc gag tC |
| 62 | cgg cct gTt gcc gag tC |
| 63 | gag tac cgg gcg gtg aG |
| 64 | gg gGc CAg gtg gac aAT |
| 65 | g gtg gac aAT tac tgc agG |
| 66 | g ggg cgg cct gat gcG |
| 67 | gag cag aAg cgg gGc CA |
| 68 | tgc aga cac aac tac ggC |
| 69 | g cgg gcc gAg gtg gG |
| 70 | t aag tGt gaG tgt cat ttc C |
| 71 | gCg cgc tAc Aac agT gaT |
| 72 | c tat aac caa gag gag GAc T |
| 73 | g cgg ttC ctg CaC aga G |
| 74 | c atc tat aac caa gag gag A |
| 75 | cac aac tac ggg gCt gTG |

Other Embodiment

The present invention may be applied to a system composed of multiple devices (such as a host computer, an interface device, a reader, and a printer) or may be applied to an apparatus composed of one device (such as a copying machine or a facsimile).

In addition, it is needless to say that the object of the present invention can also be achieved by: supplying a system or an apparatus with a storage medium recording a program code for software realizing the function of the above embodiment; and causing a computer (or CPU or MPU) in the system or the apparatus to read and execute the program code stored in the storage medium.

In this case, the program code itself read from the storage medium realizes the function of the embodiment described above, and the storage medium storing the program code constitutes the present invention.

Examples of an available storage medium for supplying a program code include a floppy (registered trademark) disk, a hard disk, an optical disk, a magneto-optical disk, a CD-ROM, a CD-R, a magnetic tape, a nonvolatile memory card, and a ROM.

The computer executes the read program code, whereby the function of the embodiment is realized. Needless to say, in addition to the case, the case where an operating system (OS) or the like operating on the computer performs part or whole of the actual processing on the basis of an instruction from the program code, and the processing allows the function of the embodiment to be realized is also included in the present invention.

It is needless to say that the following case is also included in the present invention: after the program code read from the storage medium has been written in a memory provided for a function expanding board inserted into the computer or for a function expanding unit connected to the computer, a CPU or the like provided for the function expanding board or for the function expanding unit performs part or whole of the actual processing on the basis of an instruction from the program code, and the processing allows the function of the embodiment to be realized.

According to the method of the present invention, a set of mutation elements for identifying sequences can be efficiently extracted. Therefore, it becomes possible to extract a specific element from an extremely large number of kinds of sequences without any human mistake.

As a result, the method of the present invention can be utilized for selection of a DNA probe to be used for DNA analysis and diagnosis.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2003-434554 filed on Dec. 26, 2003, which is hereby incorporated by reference herein.

What is claimed is:

1. An information processing method for acquiring and outputting information with respect to an element for discriminating a specific sequence in multiple sequence data, comprising:
   using a specifically programmed computer to perform the steps of:
   a first step of acquiring alignment data of multiple sequences in a common region as a matrix of which row vectors correspond respectively to the multiple sequences and column vectors correspond respectively to alignment positions;
   a second step of selecting a specific sequence and removing an element of any other sequences which is different from the element of the specific sequence at the same alignment position;
   a third step of comparing two column vectors arbitrarily selected from the column vectors each corresponding to the alignment position involved in the removal of an element in the second step and removing an element in one of the two column vectors if the element of the same sequence in the other column vector was removed in the second step;
   a fourth step of extracting an element which was not removed in the second and third steps and acquiring the extracted element as a candidate for a set of elements capable of discriminating the specific sequence; and
   a fifth step of comparing one of the two column vectors after subjected to the third step with any other of the column vectors involved in the removal of an element in the second step and removing an element in either one of the compared column vectors,
   wherein the second to fourth steps are repeated until only one element is left in the either one of the compared column vectors.

2. The information processing method according to claim 1, wherein the second to fifth steps are repeated by selecting any other sequence as the specific sequence, and the method further comprises a sixth step of outputting a set of elements for discriminating each specific sequence in association with the specific sequence.

3. An information processing method for acquiring and outputting information with respect to an element for discriminating a specific sequence in multiple sequence data, comprising:
   using a specifically programmed computer to perform the steps of:
   a first step of acquiring alignment data of multiple sequences in a common region as a matrix of which row vectors correspond respectively to the multiple sequences and column vectors correspond respectively to alignment positions;
   a second step of selecting a specific sequence and removing an element of any other sequences which is the same as the element of the specific sequence at the same alignment position;
   a third step of comparing two column vectors arbitrarily selected from the column vectors each corresponding to the alignment position involved in the removal of an element in the second step and removing an element in one of the two column vectors if the element of the same sequence in the other column vector was removed in the second step;
   a fourth step of extracting an element which was not removed in the second and third steps and acquiring the extracted element as a candidate for a set of elements capable of discriminating the specific sequence; and
   a fifth step of comparing one of the two column vectors after subjected to the third step with any other of the column vectors involved in the removal of an element in the second step and removing an element in either one of the compared column vectors,
   wherein the second to fourth steps are repeated until only one element is left in the either one of the compared column vectors.

4. The information processing method according to claim 3, wherein the second to fifth steps are repeated by selecting any other sequence as the specific sequence, and the method further comprises a sixth step of outputting a set of elements for discriminating each specific sequence in association with each specific sequence.

5. The information processing method according to any of claims 1, 2, 3, and 4, further comprising a step of evaluating the acquired candidate.

6. A control program stored on a computer-readable memory medium, the program to be executed by a computer for performing the method according to any of claims 1, 2 ,3, and 4.

* * * * *